US007029879B1

United States Patent
Ain et al.

(10) Patent No.: US 7,029,879 B1
(45) Date of Patent: Apr. 18, 2006

(54) IODINE UPTAKE RESTORATION IN THYROID CANCER

(75) Inventors: Kenneth B. Ain, Lexington, KY (US); Gopalakrishnan Venkataraman, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/606,042

(22) Filed: Jun. 29, 2000

Related U.S. Application Data

(60) Provisional application No. 60/140,976, filed on Jun. 29, 1999.

(51) Int. Cl.
*C12P 21/24* (2006.01)
*C12N 5/08* (2006.01)

(52) U.S. Cl. ............... 435/70.3; 435/375; 435/377

(58) Field of Classification Search ............... 514/44; 435/4, 325, 352, 366, 383, 70.3, 375, 377, 435/70.5; 424/9.1, 9.2; 536/28.1, 26.3; 524/173; 532/65
See application file for complete search history.

(56) References Cited

OTHER PUBLICATIONS

Schmutzler, C, et al, 1997, Retinoic acid increases sodium/iodide symporter mRNA levels in human thyroid cancer cell lines and suppresses expression of functional symporter in nontransformed FRTL-5, Biochem. Biophys. Res. Commun., vol. 240, pp. 832-838.*
Avvedimento, EV, et al, 1989, Reactivation of thyroglobulin gene expression in transformed thyroid cells by 5-azacytidine, Cell, vol. 58, pp. 1135-1142.*
Spath, GF, et al, Hepatocyte nuclear factor 4 expression overcomes repression of the hepatic phenotype in dedifferentiated hepatoma cells, Molecular and Cellular Biology, vol. 17, pp. 1913-1922.*
Van Herle, AJ, et al, 1990, Effects of 13 cis-retinoic acid on growth and differentiation of human follicular carcinoma cells (UCLA RO 82 W-1) in vitro, Journal of Clinical Endocrinology and Metabolism, vol. 71, pp. 755-763.*
Swafford, DS, et al, 1997, Frequent aberrant methylation of p16-INK4a in primary rat lung tumors, Molecular and Cellular Biology, vol. 17, pp. 1366-1374.*
Grunwald, F, et al, 1998, Redifferentiation therapy with retinoic acid in follicular thyroid cancer, Journal of Nuclear Medicine, vol. 39, pp. 1555-1558.*
Simon, D, et al, 1998, Redifferentiation therapy with retinoids: therapeutic option for advanced follicular and papillary thyroid carcinoma, World Journal of Surgery, vol. 22, pp. 569-574.*
Venkataraman, G, et al, 1999, Restoration of iodide uptake in dedifferentiated thyroid carcinoma: relationship to human NA+/I–symporter gene methylation status, vol. 84, pp. 2449-2457.*
Kleef, J, et al, 1998, The helix-loop-helix protein Id2 is overexpressed in human pancreatic cancer, Cancer Research, vol. 58, pp 3769-3772.*
Thomas, GA, et al, 1992, Production of thyroid tumors in mice by demethylating agents, Carcinogenesis, vol. 13, pp. 1039-1042.*
Matsuda, A, et al, 1997, A homozygous missense mutation of the sodium/iodide symporter gene causing iodide transport defect, Journal of Clinical Endocrinology and Metabolism, vol. 82, pp. 3966-3971.*
Vivaldi, A, et al, 2000, Sodium/iodide symporter gene transcript expression is not correlated with the scintigraphic imaging of both primary and metastatic thyroid tissues, Journal of Endocrinological Investigation, vol. 23, pp. 24 (meeting abstract).*
Graff, JR, et al, 1998, Distinct patterns of E-cadherin CpG island methylation in papillary, follicular, Hurthle's cell, and poorly differentiated human thyroid carcinoma, Cancer Research, vol. 58, pp. 2063-2066.*
Ormandy, CJ, et al, 1992, Transcriptional regulation of prolactin receptor gene expression by sodium butyrate in MCF-7 human breast cancer cells, Endocrinology, vol. 131, pp. 982-984.*

(Continued)

*Primary Examiner*—Karen A. Canella
(74) *Attorney, Agent, or Firm*—McDermott Will & Emery LLP

(57) ABSTRACT

A method of expressing a tumor specific therapeutic response element in a cancerous cell is disclosed in which the response element was previously blocked from expression. The method comprises the step of administering an unblocking agent to the cancerous cell harboring a gene encoding the response element, thereby resulting in the expression of the response element.

10 Claims, 7 Drawing Sheets

OTHER PUBLICATIONS

Schmitt, TL, et al, 2001, Transcriptional regulation of the human sodium/iodide symporter gene by PAX-8 and TTF-1, Expermiental and Clinical Endocrinology, vol. 109, pp. 27-31; BIOSIS database, accession No. 140752.*

Behr, M, et al, 1998, Cloning of a functional promoter of the human sodium/iodide-symporter gene, Biochemistry Journal, vol. 331, pp. 359-363.*

Riedel C, et al. Trends Biochem Sci Aug. 2001;26(8):490-6.*

Bender et al (Pharmaceutical Research, 1998, vol. 15, pp. 175-187).*

Thomas et al (Carcinogenesis, 1992, vol. 13, pp. 1039-1042).*

Hancock et al (Journal of the National Cancer Institute, 1984, vol. 72, pp. 833-840).*

Takenaga (International Journal of Cancer, 1984, vol. 34, pp. 83-89).*

Carr et al (Cancer Research, 1987, vol. 47, pp. 4199-4201).*

Cosgrove et al (Biochimica et Biophysica Acta, 1990, vol. 1087, pp. 80-86).*

Jones (Trends in Genetics, 1999, vol. 15, pp. 34-37).*

Nakagawa et al (Cancer Research, 1988, vol. 48, pp. 2096-2100).*

The abstract of Zabel et al (Histology and Histopathology, 1997, vol. 12, pp. 283-289).*

Schreck et al (Journal of Clinical Endocrinology and Metabolism, 1994, vol. 79, pp. 791-798).*

Abstract of Endean et al (FASEB Journal, 1995, vol. 9, p. A94).*

Kenneth B. Ain, Management of undifferentiated thyroid cancer, Balliere's Clinical Endocrinology and Metabolism, vol. 14, No. 4, pp. 615-629, 2000.

George J. Dover, et al., The Effects of Variable Doses of 5-Azacytidine on Fetal Hemoglobin Production in Sickle Cell Anemia, The Red Cell: Sixth Ann Arbor Conference, pp. 73-83.

Samuel Charache, et al., Treatment of sickle cell anemia with 5-azacytidine results in increased fetal hemoglobic production and is associated with nonrandom hypomethylation of DNA around the $\gamma$-$\delta$-$\beta$-Globin gene complex, Proc. Natl. Acad. Sci. USA, vol. 80, pp. 4842-4846, Aug. 1983, Medical Sciences.

Timothy J. Ley, et al. , 5-Azacytidine Selectively Increases $\gamma$-Globin Synthesis in a Patient With $\beta^+$ Thalassemia- The New England Journal of Medicine, vol. 307, No. 24.

Timothy J. Ley, DNA Methylation and Globin Gene Expression in Patients Treated with 5-Azacytidine, Globin Gene Expression and Hemotopoietic Differentiation, pp. 457-474.

* cited by examiner

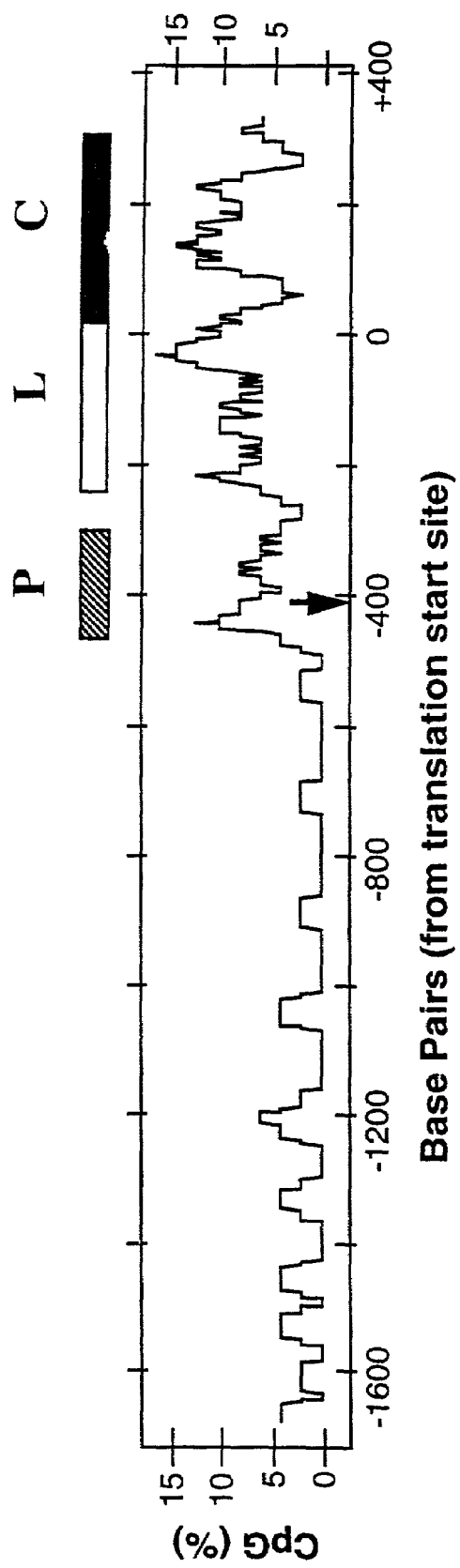

FIG. 1. CpG dinucleotide frequency in the hNIS promoter region. The DNA sequence of the hNIS promoter and its contiguous transcribed region (up to the first intron), was assessed by computer analysis. Nucleotide positions are in reference to the adenosine residue of the ATG translation start site. The bold arrow indicates the position of a 'TATA' box-like element. The shaded box (P) denotes the region of the hNIS promoter chosen for methylation analysis. The open box (L) and the solid box (C) denote the leader and coding regions, respectively, of the first exon which were analyzed for methylation status.

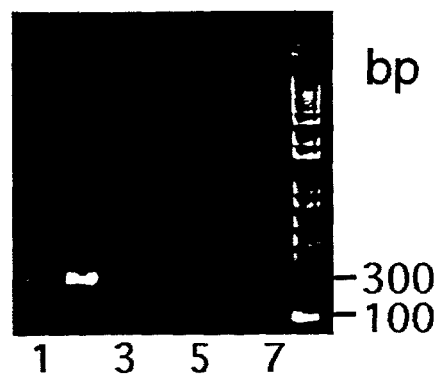
FIG. 2. hNIS mRNA expression in tall-cell papillary thyroid carcinoma. RT-PCR products were resolved on a 2% agarose gel and visualized by ethidium bromide staining. PCR substrates are: Lane 1, no cDNA (negative control); lane 2, normal thyroid (postive control); lanes 3-7, tall-cell papillary thyroid carcinomas (samples 11-15, Table 1); and lane 8, GIBCO-BRL 1 kb-plus DNA ladder.

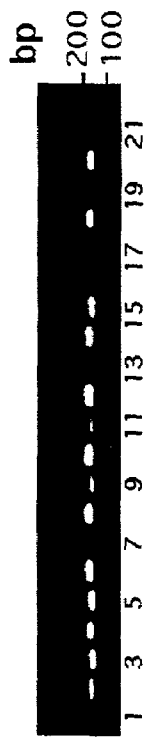

FIG. 3. Methylation analysis of the hNIS promoter in proximity to TATA box (Region P). Products of methylation specific-PCR analysis of sodium bisulfite modified genomic DNA from thyroid tumors using a methylation-specific primer pair (MET) and non-methylated-specific primer pair (UNMET) were electrophoresed on an agarose gel in adjacent lanes. Lanes 1 and 22: GIBCO-BRL 1 kb plus DNA ladder; lanes 2 through 21 (even numbered lanes contain the 151 bp UNMET product and odd numbered lanes contain the 143 bp MET product). Lane pairs starting with 2 to 12 represent the reaction pairs of tall cell papillary cancer samples 11 through 16, respectively (Table 1). Lane pairs starting with 14 through 20 represent the reaction pairs for anaplastic carcinoma (Table 1, Sample 22), negative control (no template DNA), normal thyroid and pooled human leukocyte DNA, respectively.

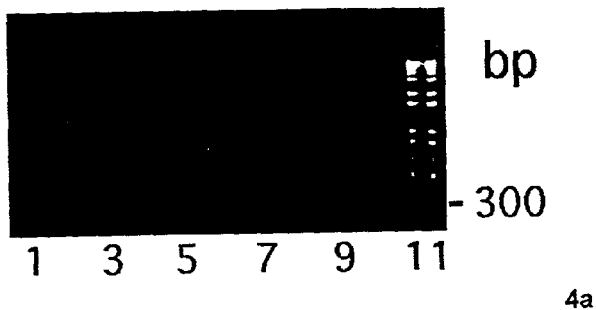

4a

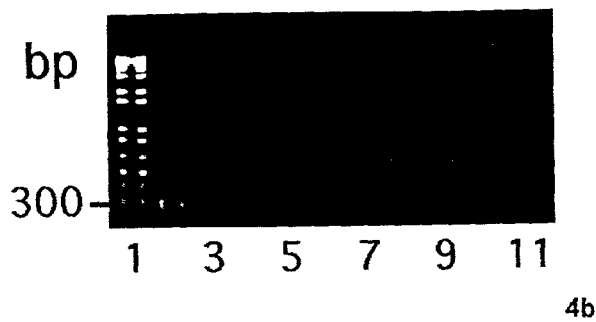

4b

FIG. 4. Re-expression of hNIS mRNA in thyroid cell lines. Follicular adenoma cell line, KAK1 (a). KAK-1 cells were treated in triplicates, with 5-azacytidine as described. The RT-PCR products were resolved on a 2% agarose gel and visualized by ethidium bromide staining. lane1. no cDNA; lane 2 to 4. untreated; lanes 5 to 7. 0.5 µM 5-azacytidine for 3 days (added each day); lanes 8 to 10. 1.0 µM 5-azacytidine for 3 days (added each day); lane 11. GIBCO-BRL 1 kb plus DNA ladder. Papillary carcinoma cell line, NPA'87 (b). NPA'87 cells were treated in triplicates, with sodium butyrate or 5-azacytidine as described. The RT-PCR products were resolved on a 2% agarose gel and visualized by ethidium bromide staining. lane1. GIBCO-BRL 1 kb plus DNA ladder; lane 2. normal human thyroid; lane 3 to 5. untreated; lanes 6 to 8. 1.0 mM sodium butyrate for 3 days; lanes 9 to 11. 1.0 µM 5-azacytidine for 3 days (added each day).

Restoration of iodide uptake in KAK-1 Cells

Restoration of iodide uptake in NPA '87 Cells

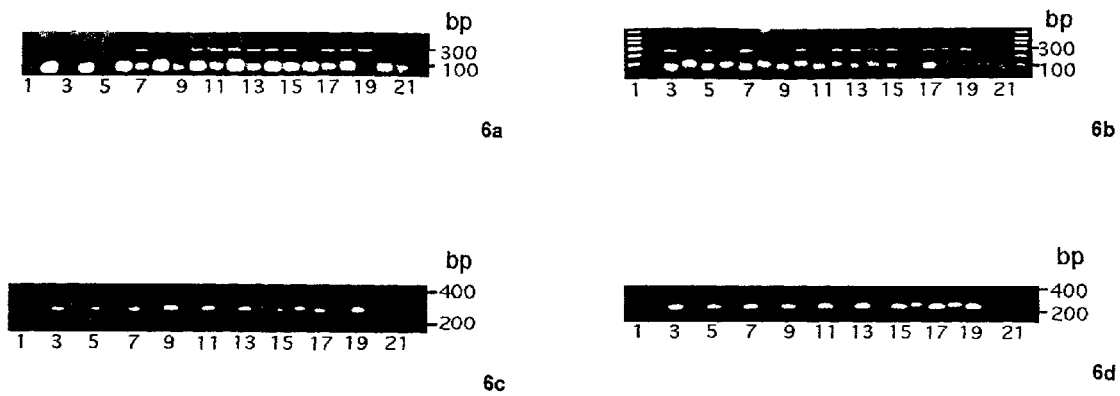

FIG. 6. Methylation analysis of hNIS gene regions in cell lines re-expressing hNIS mRNA. Products of methylation specific-PCR analysis of sodium bisulfite modified genomic DNA, from thyroid cell lines, using two methylation-specific primer pairs (MET for regions L and C) and two corresponding non-methylated-specific primer pair (UNMET for regions L and C) were elecrophoresed on an agarose gel in adjacent lanes. In all gels, lanes 1 and 22: GIBCO-BRL 1 kb plus DNA ladder; lanes 2 through 7: triplicate pairs of cell lines under basal conditions; lanes 8 through 19: triplicate pairs of cell lines in two different treatment conditions; lanes 20 and 21: negative controls without template DNA (all even numbered lanes contain the respective UNMET products and odd numbered lanes contain the correponding MET products). Cell line KAK-1 studied with primer pairs specific for region L (a). Treatment conditions in lanes 8-13 and lanes 14-19 include 5-azacytidine at 0.5 µM and 1.0 µM, respectively. Cell line KAK-1 studied with primer pairs specific for region C (b), with conditions identical to (a). Cell line NPA'87 studied with primer pairs specific for region L (c). Treatment conditions in lanes 8-13 and lanes 14-19 include sodium butyrate at 1.0 mM and 5-azacytidine at 1.0 µM, respectively. Cell line NPA'87 studied with primer pairs specific for region C (d), with conditions identical to (c).

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gtcgacatgg atctgcaaac ctcgttgctg tg                              32

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
actagttcag gtgcctttgc tttctgtcct ct                              32

<210> SEQ ID NO 3
<211> LENGTH: 353
<212> TYPE: PRT
<213> ORGANISM: Rat

<400> SEQUENCE: 3

Met Asp Leu Gln Thr Ser Leu Leu Ser Thr Gly Pro Asn Ala Ser Asn
1               5                   10                  15

Ile Ser Asp Gly Gln Asp Asn Leu Thr Leu Pro Gly Ser Pro Pro Arg
            20                  25                  30

Thr Gly Ser Val Ser Tyr Ile Asn Ile Ile Met Pro Ser Val Phe Gly
        35                  40                  45

Thr Ile Cys Leu Leu Gly Ile Val Gly Asn Ser Thr Val Ile Phe Ala
    50                  55                  60

Val Val Lys Lys Ser Lys Leu His Trp Cys Ser Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Thr Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

```
Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
            210                 215                 220

Thr Ala Ala Tyr Val Lys Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
            290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Thr
                325                 330                 335

Val Ser Asn Ala Gln Thr Ala Asp Glu Glu Arg Thr Glu Ser Lys Gly
            340                 345                 350

Thr
353

<210> SEQ ID NO 4
<211> LENGTH: 1074
<212> TYPE: DNA
<213> ORGANISM: Rat

<400> SEQUENCE: 4
gtcgacatgg atctgcaaac ctcgttgctg tccactggcc ccaatgccag caacatctcc      60
gatggccagg ataatctcac attgccgggg tcacctcctc gcacagggag tgtctcctac     120
atcaacatca ttatgccttc cgtgtttggt accatctgtc tcctgggcat cgtgggaaac     180
tccacggtca tctttgctgt ggtgaagaag tccaagctac actggtgcag caacgtcccc     240
gacatcttca tcatcaacct ctctgtggtg gatctgctct tcctgctggg catgccttc     300 atgatccacc agctcatggg gaacggcgtc tggcactttg ggaaaccat gtgcaccctc     360 atcacagcca tggacgccaa cagtcagttc actagcacct acatcctgac tgccatgacc     420
attgaccgct acttggccac cgtccacccc atctcctcca ccaagttccg gaagccctcc     480
atggccaccc tggtgatctg cctcctgtgg gcgctctcct tcatcagtat caccctgtg     540 tggctctacg ccaggctcat tcccttccca gggggtgctg tgggctgtgg catccgcctg     600
ccaaacccgg acactgacct ctactggttc actctgtacc agttttttcct ggcctttgcc     660 cttccgtttg tggtcattac cgccgcatac gtgaaaatac tacagcgcat gacgtcttcg     720
gtggccccag cctcccaacg cagcatccgg cttcggacaa agagggtgac ccgcacggcc     780
attgccatct gtctggtctt ctttgtgtgc tgggcaccct actatgtgct gcagctgacc     840
cagctgtcca tcagccgccc gaccctcacg tttgtctact gtacaacgc ggccatcagc     900 ttgggctatg ctaacagctg cctgaacccc tttgtgtaca gtgctctg tgagaccttt     960 cgaaaacgct tggtgttgtc agtgaagcct gcagcccagg ggcagctccg cacggtcagc    1020
```

```
aacgctcaga cagctgatga ggagaggaca gaaagcaaag gcacctgaac tagt      1074
```

<210> SEQ ID NO 5
<211> LENGTH: 262
<212> TYPE: RNA
<213> ORGANISM: Rat

<400> SEQUENCE: 5

```
gcgaauuggg uaccgggccc ccccucgagg ucgacgguau cgauaagcuu gauaucgaau   60
uccugcagcc cggggaucc gcccacuagu ucaggugccu uugcuuucug uccucuccuc   120
aucagcuguc ugagcguugc ugaccgugcg gagcugcccc ugggcugcag gcuucacuga   180
caacaccaag cguuuucgaa aggucucaca gagcacuaug uacacaaagg gguucaggca   240
gcuguuagca uagcccaagc ug                                           262
```

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6

```
caacagctgc ctcaaccc                                                18
```

<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7

```
cctggtgatc tgcctcct                                                18
```

<210> SEQ ID NO 8
<211> LENGTH: 1275
<212> TYPE: DNA
<213> ORGANISM: Human

<400> SEQUENCE: 8

```
taggtgatgt cagtgggagc catgaagaag ggagtgggga gggcagttgg gcttggaggc   60
ggcagcggct gccaggctac ggaggaagac cccttccca actgcggggc ttgcgctccg    120
ggacaaggtg gcaggcgctg gaggctgccg cagcctgcgt gggtggaggg gagctcagct   180
cggttgtggg agcaggcgac cggcactggc tggatggacc tggaagcctc gctgctgccc   240
actggtccca acgccagcaa cacctctgat ggccccgata acctcacttc ggcaggatca   300
cctcctcgca cggggagcat ctcctacatc aacatcatca tgccttcggt gttcggcacc   360
atctgcctcc tggcatcat cgggaactcc acggtcatct tcgcggtcgt gaagaagtcc   420
aagctgcact ggtgcaacaa cgtccccgac atcttcatca tcaacctctc ggtagtagat   480
ctcctctttc tcctgggcat gcccttcatg atccaccagc tcatgggcaa tggggtgtgg   540
cactttgggg agaccatgtg caccctcatc acggccatgg atgccaatag tcagttcacc   600
agcacctaca tcctgaccgc catggccatt gaccgctacc tggccactgt ccacccatc   660
tcttccacga gttccggaa gccctctgtg gccaccctgg tgatctgcct cctgtgggcc   720
ctctccttca tcagcatcac ccctgtgtgg ctgtatgcca gactcatccc cttcccagga   780
ggtgcagtgg gctgcggcat acgcctgccc aacccagaca ctgacctcta ctggttcacc   840
```

```
ctgtaccagt ttttcctggc ctttgccctg ccttttgtgg tcatcacagc cgcatacgtg    900
aggatcctgc agcgcatgac gtcctcagtg gcccccgcct cccagcgcag catccggctg    960
cggacaaaga gggtgacccg cacagccatc gccatctgtc tggtcttctt tgtgtgctgg   1020
gcaccctact atgtgctaca gctgacccag ttgtccatca gccgcccgac cctcaccttt   1080
gtctacttat acaatgcggc catcagcttg ggctatgcca acagctgcct caaccccttt   1140
gtgtacatcg tgctctgtga cgttccgc aaacgcttgg tcctgtcggt gaagcctgca    1200
gcccaggggc agcttcgcgc tgtcagcaac gctcagacgg ctgacgagga gaggacagaa   1260
agcaaaggca cctga                                                    1275
```

<210> SEQ ID NO 9
<211> LENGTH: 422
<212> TYPE: PRT
<213> ORGANISM: Human

<400> SEQUENCE: 9

```
MeT Ser Val Gly Ala MeT Lys Lys Gly Val Gly Arg Ala Val Gly Leu
1               5                   10                  15

Gly Gly Gly Ser Gly Cys Gln Ala Thr Glu Glu Asp Pro Leu Pro Asn
                20                  25                  30

Cys Gly Ala Cys Ala Pro Gly Gln Gly Gly Arg Arg Trp Arg Leu Pro
            35                  40                  45

Gln Pro Ala Trp Val Glu Gly Ser Ser Ala Arg Leu Trp Glu Gln Ala
        50                  55                  60

Thr Gly Thr Gly Trp MeT Asp Leu Glu Ala Ser Leu Leu Pro Thr Gly
65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile MeT
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
130                 135                 140

Asn Val Pro Asp Ile Phe Ile Ile Asn Leu Ser Val Val Asp Leu Leu
145                 150                 155                 160

Phe Leu Leu Gly MeT Pro Phe MeT Ile His Gln Leu MeT Gly Asn Gly
                165                 170                 175

Val Trp His Phe Gly Glu Thr MeT Cys Thr Leu Ile Thr Ala MeT Asp
            180                 185                 190

Ala Asn Ser Gln Phe Thr Ser Thr Tyr Ile Leu Thr Ala MeT Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285
```

```
Pro Phe Val Ile Thr Ala Ala Tyr Val Arg Ile Leu Gln Arg MeT
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
                340                 345                 350

Arg Pro Thr Leu Thr Phe Val Tyr Leu Tyr Asn Ala Ala Ile Ser Leu
                355                 360                 365

Gly Tyr Ala Asn Ser Cys Leu Asn Pro Phe Val Tyr Ile Val Leu Cys
    370                 375                 380

Glu Thr Phe Arg Lys Arg Leu Val Leu Ser Val Lys Pro Ala Ala Gln
385                 390                 395                 400

Gly Gln Leu Arg Ala Val Ser Asn Ala Gln Thr Ala Asp Glu Glu Arg
                405                 410                 415

Thr Glu Ser Lys Gly Thr
                420

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
gtcgacatgg acctggaagc ctcgctgctg c                              31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
actagttcag gtgcctttgc tttctgtcct c                              31

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agtcgacatg tcagtgggag ccatgaagaa ggg                            33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
aactagttca ggtgcctttg ctttctgtcc tct                            33

<210> SEQ ID NO 14
<211> LENGTH: 1074
<212> TYPE: DNA
```

<210> SEQ ID NO 14
<211> LENGTH: 1074
<212> TYPE: DNA
<213> ORGANISM: Human

<400> SEQUENCE: 14

| | | | | | |
|---|---|---|---|---|---|
| gtcgacatgg | acctggaagc | ctcgctgctg | cccactggtc | ccaacgccag | caacacctct | 60 |
| gatggccccg | ataacctcac | ttcggcagga | tcacctcctc | gcacgggag | catctcctac | 120 |
| atcaacatca | tcatgccttc | ggtgttcggc | accatctgcc | tcctgggcat | catcgggaac | 180 |
| tccacggtca | tcttcgcggt | cgtgaagaag | tccaagctgc | actggtgcaa | caacgtcccc | 240 |
| gacatcttca | tcatcaacct | ctcggtagta | gatctcctct | ttctcctggg | catgcccttc | 300 |
| atgatccacc | agctcatggg | caatggggtg | tggcactttg | gggagaccat | gtgcaccctc | 360 |
| atcacggcca | tggatgccaa | tagtcagttc | accagcacct | acatcctgac | cgccatggcc | 420 |
| attgaccgct | acctggccac | tgtccacccc | atctcttcca | cgaagttccg | gaagccctct | 480 |
| gtggccaccc | tggtgatctg | cctcctgtgg | gccctctcct | tcatcagcat | caccctgtg | 540 |
| tggctgtatg | ccagactcat | ccccttccca | ggaggtgcag | tgggctgcgg | catacgcctg | 600 |
| cccaacccag | acactgacct | ctactggttc | accctgtacc | agttttttcct | ggcctttgcc | 660 |
| ctgccttttg | tggtcatcac | agccgcatac | gtgaggatcc | tgcagcgcat | gacgtcctca | 720 |
| gtggcccccg | cctcccagcg | cagcatccgg | ctgcggacaa | agagggtgac | ccgcacagcc | 780 |
| atcgccatct | gtctggtctt | ctttgtgtgc | tgggcaccct | actatgtgct | acagctgacc | 840 |
| cagttgtcca | tcagccgccc | gaccctcacc | tttgtctact | tatacaatgc | ggccatcagc | 900 |
| ttgggctatg | ccaacagctg | cctcaacccc | tttgtgtaca | tcgtgctctg | tgagacgttc | 960 |
| cgcaaacgct | tggtcctgtc | ggtgaagcct | gcagcccagg | ggcagcttcg | cgctgtcagc | 1020 |
| aacgctcaga | cggctgacga | ggagaggaca | gaaagcaaag | gcacctgaac | tagt | 1074 |

<210> SEQ ID NO 15
<211> LENGTH: 1283
<212> TYPE: DNA
<213> ORGANISM: Human

<400> SEQUENCE: 15

| | | | | | |
|---|---|---|---|---|---|
| agtcgacatg | tcagtgggag | ccatgaagaa | gggagtgggg | agggcagttg | gcttggagg | 60 |
| cggcagcggc | tgccaggcta | cggaggaaga | ccccttccc | aactgcgggg | cttgcgctcc | 120 |
| gggacaaggt | ggcaggcgct | ggaggctgcc | gcagcctgcg | tgggtggagg | ggagctcagc | 180 |
| tcggttgtgg | gagcaggcga | ccggcactgg | ctgatggac | ctggaagcct | cgctgctgcc | 240 |
| cactggtccc | aacgccagca | acacctctga | tggccccgat | aacctcactt | cggcaggatc | 300 |
| acctcctcgc | acgggagca | tctcctacat | caacatcatc | atgccttcgg | tgttcggcac | 360 |
| catctgcctc | ctgggcatca | tcgggaactc | cacggtcatc | ttcgcggtcg | tgaagaagtc | 420 |
| caagctgcac | tggtgcaaca | acgtccccga | catcttcatc | atcaacctct | cggtagtaga | 480 |
| tctcctcttt | ctcctgggca | tgcccttcat | gatccaccag | ctcatgggca | atggggtgtg | 540 |
| gcactttggg | gagaccatgt | gcaccctcat | cacggccatg | gatgccaata | gtcagttcac | 600 |
| cagcacctac | atcctgaccg | ccatggccat | tgaccgctac | ctggccactg | tccacccat | 660 |
| ctcttccacg | aagttccgga | agccctctgt | ggccaccctg | gtgatctgcc | tcctgtgggc | 720 |
| cctctccttc | atcagcatca | ccctgtgtg | gctgtatgcc | agactcatcc | ccttcccagg | 780 |
| aggtgcagtg | ggctgcggca | tacgcctgcc | caacccagac | actgacctct | actggttcac | 840 |
| cctgtaccag | ttttttcctgg | cctttgccct | gccttttgtg | gtcatcacag | ccgcatacgt | 900 |
| gaggatcctg | cagcgcatga | cgtcctcagt | ggccccgcc | tcccagcgca | gcatccggct | 960 |

```
gcggacaaag agggtgaccc gcacagccat cgccatctgt ctggtcttct ttgtgtgctg   1020
ggcaccctac tatgtgctac agctgaccca gttgtccatc agccgcccga ccctcacctt   1080
tgtctactta tacaatgcgg ccatcagctt gggctatgcc aacagctgcc tcaacccctt   1140
tgtgtacatc gtgctctgtg agacgttccg caaacgcttg gtcctgtcgg tgaagcctgc   1200
agcccagggg cagcttcgcg ctgtcagcaa cgctcagacg gctgacgagg agaggacaga   1260
aagcaaaggc acctgaacta gtt                                          1283

<210> SEQ ID NO 16
<211> LENGTH: 420
<212> TYPE: RNA
<213> ORGANISM: Human

<400> SEQUENCE: 16
caaaagcugg agcuccaccg cgguggcggc cgcucuagcc cacuaguuca ggugccuuug     60
cuuucugucc ucuccucguc agccgucuga gcguugcuga cagcgcgaag cugccccugg    120
gcugcaggcu ucaccgacag gaccaagcgu uugcggaacg ucucacagag cacgauguac    180
acaaaggggu ugaggcagcu guuggcauag cccaagcuga uggccgcauu guauaaguag    240
acaaagguga gggucgggcg gcugauggac aacuggguca gcuguagcac auaguagggu    300
gcccagcaca caaagaagac cagacagaug gcgauggcug ugcggucac ccucuuuguc     360 cgcagccgga ugcugcgcug ggaggcgggg gccacugagg acgucaugcg cugcaggauc    420
```

IODINE UPTAKE RESTORATION IN THYROID CANCER

CONTINUING DATA

This application claims the benefit of priority to U.S. Provisional Application No. 60/140,976, filed Jun. 29, 1999, the contents of which are incorporated herein by reference in their entirety.

BACKGROUND OF THE INVENTION

1. Field of the Invention

The present invention relates to a method for expressing a gene product that could not be expressed because of blockage occurring in a regulatory region of the gene. The present invention also relates to a method of restoring iodide transport in cells defective in iodide transport. The present invention is also directed to a method of treating tumors by expressing tumor specific therapeutic response element in a cancerous cell in which the response element was blocked from expression.

2. Brief Description of the Related Art

The initial step in the synthesis of thyroid hormone is the active transport of iodide, mediated by the sodium-iodide symporter (NIS) located in the basolateral membrane of thyroid follicular cells (1). This iodide-concentrating ability of thyroid follicular cells is exploited for the treatment of differentiated thyroid epithelial carcinomas, using therapeutic dosages of I-131. Loss of iodide concentrating ability, in the face of distantly metastatic disease, results in significant morbidity and mortality for around 10% of patients with differentiated thyroid cancers (2). In addition, anaplastic thyroid cancers, which are unable to take up radioactive iodide and do not respond to systemic chemotherapies, are invariably fatal.

The complementary DNA sequence for human NIS (hNIS), as well as the exon-intron organization, have been revealed by Smanik et al (3,4). The cloning and characterization of a 1.3 kb region of the upstream regulatory region was reported and a minimal essential hNIS promoter that shows tissue-specific expression in a human thyroid cell line was defined (5). Other investigators have further evaluated hNIS promoter constructs (6,7). It is possible that alterations in hNIS expression, responsible for loss of iodide-concentrating ability in human thyroid cancer metastases, may correspond to changes in hNIS promoter activity. This may be similar to the loss of E-cadherin expression demonstrated in human thyroid cancer cell lines, correlating to methylation of CpG islands in the E-cadherin promoter (8). Since the hNIS promoter has CpG-rich regions, as well as additional CpG islands downstream from the transcription start site, DNA methylation may be responsible for alterations in hNIS expression. The DNA sequence corresponding to the minimal essential promoter of the gene encoding hNIS has been reported (49). The contents of this reference are incorporated herein by reference in their entirety.

Nearly half of all human genes have CpG islands associated with transcriptional start sites. Unmethylated CpG islands are seen in highly transcribed genes, while heavily methylated CpG islands inhibit transcription (9). Although overall DNA methylation is often decreased in cancers, CpG islands in critical gene promoter regions can become hypermethylated, resulting in loss of gene expression (10). Such methylation may be effective in silencing gene expression despite variable degrees of CpG site methylation from 20 to 100% (11). Laboratory and clinical studies have suggested that chemical agents may demethylate these regions and restore gene expression. Examples include use of: 5-azacytidine to restore expression of $O^6$-methylguanine-DNA methyltransferase in human cervical, brain, and colon carcinomas (12,13); phenylacetate to induce fetal hemoglobin expression in human leukemic cells (14); and sodium butyrate to induce prolactin receptor expression in human breast cancer cells (15).

The present invention is directed to a method of controlling transcriptional expression of a gene by a multi-faceted epigenetic approach. That is, the gene of interest is transcriptionally regulated by modifying the chromosome structure without mutating the bases in the DNA. Several examples of epigenetic modifications of the chromosome are included in the invention, without limitation. Administration of butyrate, for example, results in the acetylation of histones, thereby resulting in a more "open" chromatin structure facilitating transcriptional activation (50–52). Phosphorylation of the nucleosome similarly alters the chemical and physical properties of the nucleosome, thereby allowing greater or lesser access to a specific trans- acting factor that may bind to a specific region on the DNA (55–56). Also, administration of certain critical amounts of endogenous or exogenous DNA binding agents, such as polyamines, cause the level of transcriptional activity of a gene to alter in part because of the change in the chemical and physical properties of the modified nucleosome (53–54). Thus, it can be seen that the methods of demethylating or inhibiting methylation of DNA, as exemplified herein, serves as merely an illustration of transcriptional regulation engendered by epigenetic modification of chromosomes.

In the present invention methylation of the characterized hNIS promoter, and potentially regulatory downstream regions, and their correlation with loss of hNIS mRNA expression, as well as clinical loss of iodide uptake, in samples of thyroid tumor tissues were tested. In addition, using human thyroid carcinoma cell lines and putative demethylation agents, the reversibility of loss of hNIS mRNA expression and functional activity, measured as iodide uptake were evaluated.

SUMMARY OF THE INVENTION

The present invention is also directed to a method of expressing a tumor specific therapeutic response element in a cancerous cell in which the response element was blocked from expression, comprising the step of administering an unblocking agent to the cancerous cell harboring a gene encoding the response element, thereby resulting in the expression of the response element.

The gene of interest may be a gene that is endogenous to the cancerous cell, or may be exogenous to the cancer cell, as introduced to the cancer cell by transfection technique, for example. Preferably, the gene encodes a sodium-iodide symporter (NIS). More preferably, the gene may encode a human sodium-iodide symporter (hNIS).

The cell may be any cancerous cell, but is preferably a thyroid-derived cell. More preferably, the cells are dedifferentiated. In the present invention, a tumor specific therapeutic response element that was turned off during dedifferentiation is caused to be re-expressed. The tumor specific therapeutic response element may be a tumor specific antigen that may serve as a target for a therapeutic antibody, or it may be an iodine transporter such that radioactive iodine may be captured and retained in the cancerous cells. The tumor specific therapeutic response element may be any factor that is specifically expressed by cancerous cells and may serve as a specific target for therapy, and therefore is not limited to the particular forms exemplified herein.

The blockage of transcriptional activation of the tumor specific therapeutic response element can occur in a variety of ways. One of these ways is through DNA methylation of certain sequence in or near the regulatory region, the promoter, or the coding sequence. Preferably, CpG islands that may be present are the sites of methylation. The present invention exemplifies demethylation as a method of activating transcription of a gene. But the invention is not limited to the demethylation method alone. Other methods include inhibiting the methylation of DNA sequences. The demethylating agent may be any chemical or enzymatic compound or mechanism that demethylates nucleic acids, and is preferably, but not limited to, dimethylsulfoxide, sodium butyrate, phenylacetate, or 5-azacytidine. The demethylating agent may also include a compound that inhibits DNA-methyltransferase activity. Furthermore, the unblocking agent may include a compound that directly inhibits methylation of a DNA sequence, or indirectly inhibits methylation by an agent that depletes polyamines. Preferably, the agent inhibits the synthesis of polyamines include, but not limited to, difluoromethylornithine(DFMO) and adenosyl-1,8-diamino-3-thio-octane.

The present invention is also directed to a method of restoring iodide transport to dedifferentiated thyroid cancer cells comprising the step of administering a demethylating agent in an amount effective to transcriptionally activate a tumor specific therapeutic response element in a cell that is defective in iodide transport. Preferably, the tumor specific therapeutic response element is the sodium iodide symporter.

Another object of the invention is to provide a demethylating or methylation inhibiting agent that can transcriptionally activate or unblock the expression of the trans- acting factor specific for the regulation of the specific therapeutic response element. This further extends to the expression of other trans- acting factors in the regulatory cascade.

The present invention is also directed to a method of treating a tumor by expressing a tumor specific therapeutic response element in a cancerous cell in which the response element was blocked from expression, which comprises the steps of:
  a) administering an unblocking agent to the cancerous cell harboring a gene encoding the response element, thereby resulting in the expression of the response element; and
  b) administering a therapeutic substance to target said tumor specific therapeutic response element.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given hereinbelow, and the accompanying drawings which are given by way of illustration only, and thus are not limitative of the present invention, and wherein;

FIG. 1 shows CpG dinucleotide frequency in the hNIS promoter region. The DNA sequence of the hNIS promoter and its contiguous transcribed region (up to the first intron), was assessed by computer analysis. Nucleotide positions are in reference to the adenosine residue of the ATG translation start site. The bold arrow indicates the position of a 'TATA' box-like element. The shaded box (P) denotes the region of the hNIS promoter chosen for methylation analysis. The open box (L) and the solid box (C) denote the leader and coding regions, respectively, of the first exon which were analyzed for methylation status.

FIG. 2 shows hNIS mRNA expression in tall-cell papillary thyroid carcinoma. RT-PCR products were resolved on a 2% agarose gel and visualized by ethidium bromide staining. PCR substrates are: Lane 1, no cDNA (negative control); lane 2, normal thyroid (positive control); lanes 3–7, tall-cell papillary thyroid carcinomas (samples 11–15, Table 1); and lane 8, GIBCO-BRL 1 kb-plus DNA ladder.

FIG. 3 shows methylation analysis of the hNIS promoter in proximity to TATA box (Region P). Products of methylation specific-PCR analysis of sodium bisulfite modified genomic DNA from thyroid tumors using a methylation-specific primer pair (MET) and non-methylation-specific primer pair (UNMET) were electrophoresed on an agarose gel in adjacent lanes. Lanes 1 and 22: GIBCO-BRL 1 kb plus DNA ladder; lanes 2 through 21 (even numbered lanes contain the 151 bp UNMET product and odd numbered lanes contain the 143 bp MET product). Lane pairs starting with 2 to 12 represent the reaction pairs of tall cell papillary cancer samples 11 through 16, respectively (Table 1). Lane pairs starting with 14 through 20 represent the reaction pairs for anaplastic carcinoma (Table 1, Sample 22), negative control (no template DNA), normal thyroid and pooled human leukocyte DNA, respectively.

FIGS. 4a, b. shows re-expression of hNIS mRNA in thyroid cell lines. Follicular adenoma cell line, KAK1 (a). KAK-1 cells were treated in triplicates, with 5-azacytidine as described. The RT-PCR products were resolved on a 2% agarose gel and visualized by ethidium bromide staining. lane 1. no cDNA; lane 2 to 4. untreated; lanes 5 to 7. 0.5 µM 5-azacytidine for 3 days (added each day); lanes 8 to 10. 1.0 µM 5-azacytidine for 3 days (added each day); lane 11. GIBCO-BRL 1 kb plus DNA ladder. Papillary carcinoma cell line, NPA'87 (b). NPA'87 cells were treated in triplicates, with sodium butyrate or 5-azacytidine as described. The RT-PCR products were resolved on a 2% agarose gel and visualized by ethidium bromide staining. lane 1. GIBCO-BRL 1 kb plus DNA ladder; lane 2. normal human thyroid; lane 3 to 5. untreated; lanes 6 to 8. 1.0 mM sodium butyrate for 3 days; lanes 9 to 11. 1.0 µM 5-azacytidine for 3 days (added each day).

Figure 5A:
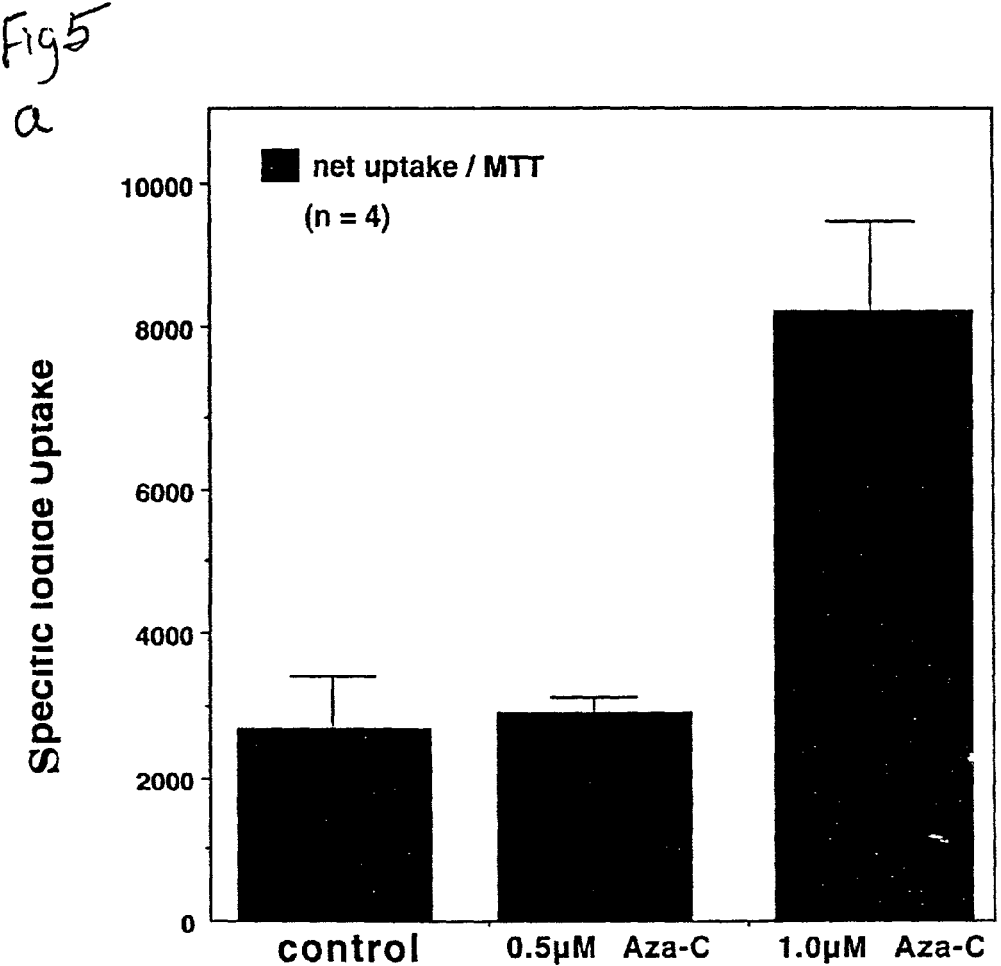
Figure 5:
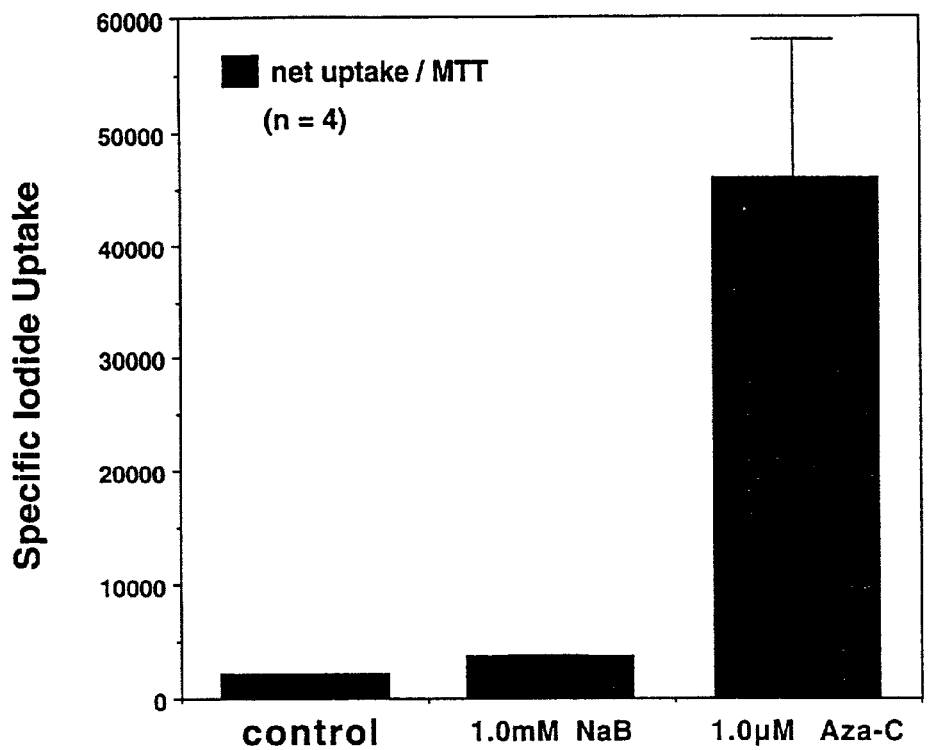

FIGSS. 5a, b. shows restoration of iodide uptake in neoplastic thyroid cell lines. The uptake values are normalized for cell viability, as determined by the MTT assay in a parallel set of plates. Follicular adenoma cell line, KAK-1 (a). The KAK-1 cells were treated with 5-azacytidine and the iodide uptake was measured, in quadruplicates, as described. Papillary carcinoma cell line, NPA'87 (b). The NPA'87 cells were treated with sodium butyrate or 5-azacytidine and the iodide uptake was measured, in quadruplicates, as described.

FIGS. 6 a–d. shows methylation analysis of hNIS gene regions in cell lines re-expressing hNIS mRNA. Products of methylation specific-PCR analysis of sodium bisulfite modified genomic DNA, from thyroid cell lines, using two methylation-specific primer pairs (MET for regions L and C) and two corresponding non-methylated-specific primer pair (UNMET for regions L and C) were electrophoresed on an agarose gel in adjacent lanes. In all gels, lanes 1 and 22: GIBCO-BRL 1 kb plus DNA ladder; lanes 2 through 7: triplicate pairs of cell lines under basal conditions; lanes 8 through 19: triplicate pairs of cell lines in two different treatment conditions; lanes 20 and 21: negative controls without template DNA (all even numbered lanes contain the respective UNMET products and odd numbered lanes contain the corresponding MET products). Cell line KAK-1 studied with primer pairs specific for region L (a). Treatment conditions in lanes 8–13 and lanes 14–19 include 5-azacytidine at 0.5 µM and 1.0 µM, respectively. Cell line KAK-1 studied with primer pairs specific for region C (b), with conditions identical to (a). Cell line NPA'87 studied with primer pairs specific for region L (c). Treatment conditions in lanes 8–13 and lanes 14–19 include sodium butyrate at 1.0 mM and 5-azacytidine at 1.0 µM, respectively. Cell line NPA'87 studied with primer pairs specific for region C (d), with conditions identical to (c).

DETAILED DESCRIPTION OF THE INVENTION

As used herein, "block", "blocking" or "blockage" means the inhibition or transcription of a gene of interest. The inhibition includes, but is not limited to, methylation of certain regions on the gene of interest. The region methylated on the gene includes the promoter, other regulatory regions, and the coding sequence. It is to be understood that the term "blockage" encompasses inhibition of a gene's expression by any means. This includes the context of a gene of interest not being expressed because its specific transacting factor is either not made or is non-functional.

As used herein, "unblock(s)" means the transcriptional activation or expression of a gene which was previously inhibited from being expressed. The activation may be caused by, but is not limited to, demethylation or inhibition of methylation of the relevant regions on the gene.

As used herein, "regulatory sequence" or "regulatory region" refers to a non-coding portion of a gene which regulates activation or expression of the gene product. The regulatory sequence may include, but is not limited to, the promoter, as well as certain DNA sequences upstream of the promoter that are cis- acting regions for binding by transacting factors. Regulatory sequences may exist near or at the downstream end of the gene, or even in the middle of the gene in the form of introns.

Treatment of metastatic thyroid carcinoma requires effective systemic agents. Due to the absence of applicable chemotherapeutics, radioiodine therapy is the only efficacious modality. The failure to respond to radioiodine portends grave consequences and is an appropriate target for correction. Loss of hNIS gene expression appeared a likely cause for loss of iodide concentrating ability; however the inventors have demonstrated that some thyroid cancers maintain expression of hNIS mRNA despite loss of function, suggesting diverse pathophysiology. This was of particular surprise for anaplastic carcinomas since these tumors do not have clinical iodide uptake (5). In those tumors in which loss of hNIS mRNA was observed, potential mechanisms were explored, focusing on reversible etiologies.

Some investigators have attempted to restore iodide uptake using retinoids. A nominal increase in iodide uptake activity was reported in a thyroid follicular carcinoma cell line UCLA RO 82 W-1 (WRO82), treated with 13cis-retinoic acid (cRA) (27). Direct evidence of the effects of cRA on re-establishing iodide uptake in dedifferentiated follicular and papillary thyroid cancers was first reported by Simon et al (28). The latest details of their study revealed that only 14 patients (out of 20 study patients) did not concentrate any radioiodine in metastatic tumors at baseline, with only one such patient re-establishing distinct iodide uptake after cRA treatment (an additional three patients gained "weak" uptake) (29). A case report suggests a positive response to similar treatment in a single patient (30). Alternatively, a minimal enhancement of iodide uptake with gamma interferon was suggested in several human thyroid cancer cell lines in vitro (31). The mechanism for effects on iodide transport is unknown for both of those agents although they suggest that loss of hNIS activity may be a reversible phenomenon.

In view of the multiplicity of mechanisms causing loss of iodide transport, the inventors further evaluated the subset of tumors with apparent hNIS transcriptional failure and the relationship to CpG island methylation in the region of the hNIS promoter. This was of particular importance in tall-cell variant papillary thyroid cancers since nearly half of such patients lose clinical iodide transport (32,33), and the inventors show this to be a consequence of hNIS transcriptional failure. The ability of 5-azacytidine to induce hNIS mRNA, as well as iodide uptake, in thyroid carcinoma cell lines devoid of basal hNIS mRNA expression, further implicated methylation as a likely mechanism. In these cell lines, reversal of basal methylation of the L and C regions appeared associated with de novo induction of hNIS expression. On the other hand, lack of expression of hNIS mRNA in tall-cell variant papillary carcinoma tumors was not able to be assuredly explained by such methylation patterns. Part of the reason may relate to heterogeneity of cell methylation patterns between cells in the same culture. This may relate to the heterogeneity of hNIS protein expression demonstrated in normal and malignant thyroid tissues (34,35). A similar mechanism has been invoked for expression of $p16^{INK4a}$ in thyroid carcinoma cell lines and tumors (36). Likewise, tumor tissue samples are inherently heterogeneous as mixtures of tumor cells, fibroblasts, endothelial cells, smooth muscle cells, and infiltrating host immune cells. It is also possible that the specific sites of methylation responsible for loss of hNIS transcription, in or near the hNIS gene, may be different from the particular sites analyzed in this study.

Alternative explanations for loss of hNIS mRNA expression may relate to methylation of thyroid-specific transcription factor genes causing loss of transcription factor expression with indirect loss of hNIS mRNA expression. This was indicated by the KAT-5 and KAT-10 responses to 5-azacytidine treatment with acquisition of parallel TTF-1 and hNIS mRNA expression. Failure to express sufficient TTF-1 and PAX-8 can result in decreased activity of the thyroglobulin gene promoter in human thyroid carcinoma cells (37), a likely feature of the hNIS gene. Since additional, possibly complex, processes may affect post-transcriptional hNIS function, there are multiple opportunities for gene methylation to reduce iodide transport.

There are several examples of DNA methylation altering expression of thyroid-specific genes. In transgenic mice carrying the chloramphenicol acetyltransferase (CAT) gene under control of a bovine thyroglobulin promoter, CAT expression was limited to the thyroid glands and was related to thyroid-specific demethylation of the bovine thyroglobulin promoter (41). In another example, the transformed rat thyroid cell line, FRT, is unable to express its native TSH receptor gene, consequent to methylation of its promoter (42). Avvedimento et al (43,44) have shown that transformation of a rat thyroid cell line, which activated the RAS oncogene, resulted in loss of activity of the thyroglobulin gene promoter, as well as loss of expression of a thyroid-specific trans-acting factor (presumably TTF-1). Treatment with 5-azacytidine restored both TTF-1 expression and thyroglobulin promoter activity. Such cases provide evidence that thyroidal tissues use methylation as a regulatory mechanism for gene expression, particularly in transformed phenotypes.

The potential to restore iodide transport in dedifferentiated thyroid carcinomas with demethylation agents suggests clinical application. The degree of hNIS expression needed to deliver tumoricidal radioiodide is not clear. Normal thyroid tissue, stimulated by TSH, concentrates radioiodide at 1% of the administered dose per gram of tissue. Differentiated thyroid cancer metastases typically concentrate radioiodide at 0.06 to 0.3% of the administered radioiodide dose per gram of tumor (45). Calculations of the degree of radioiodide uptake and biologic residence time needed for sufficient therapy of thyroid cancer suggest that (employing an effective half-life of at least 4.5 days) tumor destruction can be achieved despite an uptake of only 0.1%, using administered activities of 300 mCi (46). Use of radioiodide dosimetry analysis, to verify upper safety margins of administered doses, may permit therapy doses exceeding 600 mCi (47) so that tumors with less than 0.05% uptake may respond to treatment. For this reason, restoration of hNIS activity sufficient to treat thyroid cancer does not require hNIS expression to the levels seen in normal human thyroid follicular cells.

Effective radioiodide therapy requires more than a functional hNIS gene. There should be sufficient expression of TSH receptors and downstream signal transduction machinery to amplify hNIS expression when TSH levels rise. In addition, failure to organify radioiodide compromises I-131 residence time in thyroid carcinoma cells, permitting radioiodide efflux and insufficient radiation delivery. This was seen by Shimura et al (48) when they transfected transformed rat thyroid cells, lacking endogenous NIS expression, with rat NIS cDNA and restored radioiodide uptake. The Shimura et al. reference is incorporated herein by reference in its entirety. Despite high levels of I-131 uptake in xenografts of these cells, they were unable to obtain tumoricidal effects due to rapid radioiodide efflux from lack of effective organification. Demethylation therapy may be able to restore additional critical functions, such as organification, downstream from iodide transport.

The following examples are offered by way of illustration of the present invention, and not by way of limitation.

EXAMPLES

Example 1

Materials and Methods

Cell Lines and Human Tissues

Human thyroid cell lines used were: MRO87 and WRO82 (both follicular carcinomas), NPA'87 (papillary carcinoma), KAT-5 and KAT-10 (both papillary carcinomas (16)), KAK-1 (benign follicular adenoma (17)), and KAT-7 (benign follicular hyperplasia). Cultures were previously treated with medium containing D-valine (18) and cis-4-hydroxy-L-proline (19) to ensure the absence of fibroblasts. Human thyroid tissues were obtained from fresh surgical samples (approved by University of Kentucky Institutional Review Board). Some tumor samples were supplied by the Cooperative Human Tissue Network (Philadelphia, Pa.) and some were obtained from surgical samples at the Clinical Center, National Institutes of Health, Bethesda, Md. (under approved protocol).

Cell Culture

Cell lines, for evaluation of iodide-uptake and hNIS expression, were grown in phenol-red-free RPMI 1640 with 5% fetal bovine serum (FBS), 100 nM sodium selenite and 0.1 nM bovine TSH (basal medium) (20). They were plated at a density of $3-5\times10^4$ cells/9.4 $cm^2$, in triplicate in basal medium, and grown for 2–3 days at 37° C. in 5% $CO_2$. They were treated with dimethylsulfoxide (DMSO, 25 µM daily for 3 days), sodium butyrate (0.5 or 1.0 mM), phenylacetate (pH 7.0, 5 or 10 mM) or 5-azacytidine (0.5 or 1.0 µM, in 25 µM DMSO, daily for 3 days) until control cells were 80% confluent (3–4 days), then changed to fresh basal medium and grown for an additional 24 hrs.

Analysis of CpG Content in the hNIS Gene Sequence

The hNIS gene sequence of the 5' flanking region (5) and the contiguous transcribed region extending up to the first intron (3,4), was analyzed using WINDOW and STATPLOT computer programs (Genetics Computer Group, Madison, Wis.) to denote CpG dinucleotide frequencies.

Nucleic Acid Isolation and Amplification

Total RNA and genomic DNA from: normal human thyroid, thyroid tumors, and cell lines (treated with agents described above), were isolated by the acid-guanidinium-phenol-chloroform method (21). All surgical samples were snap-frozen and stored at −80° C. until processed by homogenization in Trizol reagent (Life Technologies, Gaithersburg, Md.) while still frozen. Complementary DNA (cDNA) was synthesized from 1.0 µg of total RNA using MMLV reverse transcriptase (RT) with random-hexamer primers (Clontech, Palo Alto, Calif.). Each 50 µL polymerase chain reaction (PCR) vessel contained: 60 mM Tris HCl, pH 9.0, 15 mM ammonium sulfate, 3.5 mM $MgCl_2$ (1.5 mM for hTTF-1), 250 µM dNTPs (Boehringer-Mannheim, Indianapolis, Ind.), 0.2 µM each primer pair, 1 U AmpliTaq DNA polymerase (Perkin-Elmer, Norwalk, Conn.), 0.2 µg TaqStart Antibody (Clontech) and 3% cDNA. β-actin amplification (primers, Stratagene, La Jolla, Calif.) confirmed cDNA integrity, purity, and template equivalence for semiquantification. PCR primers (upstream 5' to 3'/downstream 5' to 3', in all cases) used for amplification were, for hNIS (5), CTGC-CCCAGACCAGTACAT GCC (SEQ ID NO. 1)/TGACG-GTGAAGGAGCCCTGAAG (SEQ ID NO. 2) (to amplify a coding region spanning four introns (4) yielding a 303 bp product from cDNA) and for Pax-8, AAGTCCAGCAT-TGCGGCACA (SEQ ID NO. 3)/GAGGGAAGTGCT-TATGGTCC (SEQ ID NO. 4)((22) to amplify a 329 bp product). Amplification conditions for hNIS and Pax-8 were: denaturation (95° C.×5 min); 40 cycles of 20 sec at 95° C. and 60 sec at 68° C.; followed by extension at 72° C. for 3 min. The hTTF-1 product was amplified with intron spanning primers, GCCGTACCAGGACACCATGAG (SEQ ID NO. 5)/CAGGTACTTCTGTTGCTTGAAG (SEQ ID NO. 6), which amplify a 263 bp fragment. The conditions were: 95° C. for 5 min; 45 cycles of 95° C. for 20 sec, 60° C. for 60 sec, and 72° C. for 30 sec; followed by extension at 72° C. for 3 min. The RT-PCR products were resolved on 2% agarose gels and visualized by ethidium bromide staining.

Methylation-Specific Polymerase Chain Reaction (MS-PCR) Analysis

This method utilizes PCR primer pairs to distinguish methylated from unmethylated DNA in bisulfite-modified target DNA, in which bisulfite converts unmethylated cytosines to uracil (23,24). Genomic DNAs, from normal and tumoral human thyroid tissues and cell lines, were isolated by standard techniques (21) and 1.0 µg aliquots were denatured by NaOH (10 min at 37° C.), then treated with 10 mM hydroquinone and 3.0 M sodium bisulfite (pH 5.0 under mineral oil for 16 hrs at 50° C.). Modified DNA was purified on a resin column (Qiagen) and further treated with 0.3 N NaOH for 5 min prior to ethanol precipitation. The PCR mixture contained 16.6 mM ammonium sulfate, 67 mM Tris-HCl (pH 8.8), 6.7 mM $MgCl_2$, 10 mM β-mercaptoethanol, 1.25 mM dNTPs, 0.2 µL TaqStart antibody, 1 U AmpliTaq DNA polymerase, 10 pmoles each of sense and antisense methylation-specific primers, and 50 mg of bisulphite-modified DNA target. Primers used for analysis of the hNIS promoter CpG island methylation were selected for cytosine-rich regions, containing CpG dinucleotides near the 3' end of the primers, hNIS-MET-P (sense, 5' to 3', TTAG-GTTTGGAGGCGGA GTCGC (SEQ ID NO. 7) and antisense, 5' to 3', ACCGACTATCTATCCCT CTC-CCTAAACG) (SEQ ID NO. 8) for a 143 bp product from methylated DNA and hNIS-UNMET-P (sense, 5' to 3', TTGTTTTTAGGTTTGGAGGTG GAGTTGT (SEQ ID NO. 9) and antisense, 5' to 3', CAACCAACTATCTATC-CCTCTC CCTAAACA) (SEQ ID NO. 10) for a 151 bp product from unmethylated genomic DNA. Additional sets of primers were similarly designed to analyze further downstream elements. They were: hNIS-MET-L (sense, ATA-GATAGATAGTAGGGGCGGAC (SEQ ID NO. 11) and antisense, GACCT CCATAAAAACGAATACG) (SEQ ID NO. 12) for a 265 bp product, with hNIS-UNMET-L (sense, TAGGATAGATAGATAGTAGGGGTGGAT (SEQ ID NO. 13), and antisense, CTCCACAACCTCCATAAAAA-CAAATACA) (SEQ ID NO. 14), for a 275 bp product, hNIS-MET-C (sense, AGGTCGTGGAGATCGGGGAAC (SEQ ID NO. 15) and antisense, ACGATAAACCTCCGAC-GACACG) (SEQ ID NO. 16) for a 242 bp product, and hNIS-UNMET-C (sense, TTATGGAGGTTGTGGAGAT-TGGGGAAT (SEQ ID NO. 17), and antisense, CATAA-CAATAAACCTCCAACAACACA) (SEQ ID NO. 18), for a 252 bp product. The amplification conditions were: Taq polymerase activation at 95° C. for 5 min, 40 cycles of: denaturation at 94° C. for 20 s, annealing at 60° C. for 30 s and polymerization at 72° C. for 30 s. MS-PCR products were resolved by agarose gel electrophoresis and visualized by ethidium bromide staining and UV transillumination.

Iodide Uptake Assay

Cell lines, treated with differentiation agents and control cultures, were washed with 2 mL of buffer containing: 10 mM HEPES (pH 8.3), 5.5 mM glucose, 5.4 mM KCl, 1.3 mM $CaCl_2$, 0.4 mM $Na_2HPO_4$, 0.44 mM $KH_2PO_4$, and either 137 mM NaCl (Buffer A) or 100 mM choline chloride (Buffer B). After a 60 min incubation in the same buffer supplemented with Na($^{125}$I) (1.0 µCi/2 mL) and 1.0 µM NaI, cells were washed once with Buffer A, lysed with 0.1 M NaOH and gamma counted (5). A parallel set of dishes, similarly plated and treated, were used for normalization of uptake activity, using 3-(4,5-dimethylthiazol-2-yl)-2,5-diphenyltetrazolium bromide (MTT) assay (25) as an index of cell viability. Gamma counts of cells incubated in Buffer B were subtracted from counts of cells incubated in Buffer A, under corresponding conditions, to account for non-specific binding of radioiodide.

Clinical Radioiodine Uptake

Assessment of radioiodine uptake in clinical tumor samples was based upon the results of I-131 whole body scans (using 5 mCi I-131 tracer doses), performed 6–8 weeks after excision of the primary tumor during surgical thyroidectomy. The presence of radioiodine uptake in metastatic tumor deposits was presumed to be indicative of positive radioiodine uptake in the primary tumor sample. This is based upon the assumption that tumor redifferentiation, spontaneously restoring loss of iodide uptake, is far less common than tumor dedifferentiation. The absence of radioiodine uptake in palpable or radiologically discernible tumor metastases was presumed to reflect loss of radioiodine uptake in the primary tumor sample. This designation is likely correct; however it is possible that metastases may have less functionality than their parent tumors. In the absence of persistent tumor metastases, the assessment of radioiodine uptake was not possible. Some tumor samples were obtained from recurrent tumors which had been documented to lack radioiodine uptake on the basis of previous whole body scanning.

Example 2

Results

CpG Dinucleotide Distribution in the Context of the hNIS Promoter

The hNIS promoter region, and its contiguous downstream regions up to the first intron, were analyzed for the presence of CpG islands. The frequency plot (FIG. 1) shows a region of the promoter, surrounding the transcription start site (5) and extending upstream for about 100 base pairs, to be rich in CpG dinucleotides (region P). This was the only upstream region in the characterized promoter that was CpG-rich. Sequence comparison revealed that this region shared significant homology to the rat NIS promoter region (26). This region was selected for analysis of methylation status in clinical tumors and cell lines. Additional CpG-rich sequences are present downstream from this region, extending to the first intron. Regions L and C, selected for methylation analysis, corresponded to CpG-rich sequences in the hNIS leader and coding regions, respectively, within the first exon.

hNIS mRNA expression and Clinical Iodide Uptake in Thyroid Carcinoma

Primary thyroid tumors were analyzed by RT-PCR for the expression of hNIS mRNA (FIG. 2 and Table 1). Messenger RNA for hNIS was poorly expressed in all of six tall cell papillary carcinomas, ranging from undetectable in four tumors and moderately positive in two tumors (five cases shown in FIG. 2). In contrast, hNIS mRNA expression was clearly detectable in both of the follicular carcinomas, 9 of 10 typical papillary carcinomas (variable levels of expression), and in both of two anaplastic thyroid carcinomas. Two of the three Hürthle cell carcinomas were negative for hNIS mRNA expression. Among the 19 tumor samples which were able to be assessed for clinical radioiodide uptake, 13 cases exhibited concordance of hNIS mRNA expression with whole body scanning (7 with concordant positive findings and 6 with concordant negative findings). In 6 cases (dispersed between all of the tumor histologies except follicular carcinoma) there was no detectable radioiodine uptake on whole body scanning despite detectable hNIS mRNA in the tumor sample. Analysis of thyroid transcription factor mRNA expression in these discordant cases revealed that all expressed PAX-8 and only 2 of the 6 cases expressed TTF-1. Since only one of 7 tumor samples, with concordant positive radioiodine uptake and hNIS mRNA expression, lacked TTF-1 mRNA expression, loss of this factor may contribute to loss of hNIS function, but is not totally explanatory.

Methylation Status and hNIS mRNA Expression in Thyroid Cancers

The NIS promoter was only faintly methylated in normal human thyroid tissues and in pooled human white blood cells. As described in the previous section, hNIS mRNA was undetectable in four out of six tall cell papillary carcinomas and low in the other two. In all of these six cases the hNIS promoter (region P) was strongly methylated (FIG. 3 and Table 1). Region L was methylated in all but one case, although displaying lower signal intensities for the methylated amplification product. A CpG-rich segment of the coding region (Region C) displayed heterogeneous methylation among tall cell tumors, without any particular correlation to hNIS mRNA expression. However, of the ten papillary thyroid tumors, there was no apparent association of methylation, in Regions P, L, or C, with loss of hNIS mRNA expression. Likewise, although both follicular carcinomas expressed hNIS mRNA, they each showed different methylation patterns between the regions. All of the three cases of Hürthle cell carcinoma had unmethylated hNIS promoter regions, and variably methylated L and C regions, but only one of them expressed hNIS mRNA.

Treatment of Thyroid Carcinoma Cell Lines to Restore Expression of hNIS mRNA and Effect on Iodide Uptake Seven human thyroid neoplastic cell lines, devoid of hNIS mRNA expression under basal monolayer conditions, were treated with putative chemical demethylation agents in an attempt to restore hNIS expression. These cell lines were derived from three papillary carcinomas (NPA'87, KAT-5, and KAT-10), two follicular carcinomas (WRO82 and MRO87) and two benign follicular neoplasms (KAK-1 and KAK 50) (5). Three different demethylation or redifferentiation agents (viz., sodium butyrate, phenylacetate and 5-azacytidine) were tested on each of 7 cell lines for their ability to induce re-expression of hNIS mRNA. Re-expression of hNIS mRNA was achieved in all three of the papillary cell lines and one of the benign follicular adenomas under at least one treatment condition (Table 2). FIG. 4, a and b, demonstrate the hNIS mRNA re-expression in cell lines KAK-1 and NPA'87, respectively.

To investigate whether re-expression of NIS mRNA is sufficient to restore hNIS function, i.e., iodide uptake, we treated responding cells under the same conditions as used to restore mRNA expression and analyzed for $^{125}I$ uptake activity. Of the four responding cell lines tested, there was a greater than two-fold increase in uptake in KAK-1 cells (derived from a benign follicular adenoma) when treated with 1.0 μM 5-azacytidine as compared with untreated cells (FIG. 5a). However, no enhancement of uptake was seen using 0.5 μM 5-azacytidine, even though re-expression of hNIS mRNA was comparable under the two different concentrations of 5-azacytidine (FIG. 4a). The iodide uptake activity in NPA'87 cells (derived from a papillary carcinoma) was slightly increased with 1.0 mM sodium butyrate while 1.0 M 5-azacytidine treatment resulted in over 15-fold increased uptake (FIG. 5b). As in the other cell line, the differences in iodide uptake were noted despite similar expression of hNIS mRNA (FIG. 4b), suggesting the possible contribution of some other inducible factor.

Restoration of Iodide Uptake and Demethylation of hNIS Promoter

The cell lines KAK-1, KAT-5, KAT-10 and NPA'87, in which hNIS expression was restored, were grown under basal and re-expression conditions and the DNA were analyzed for their methylation status at the same three gene regions as studied in the tumors (Table 2). This analysis revealed that the P region was unmethylated under all conditions, basal or otherwise. Methylation of the L and C regions, under basal conditions, was clearly evident in all four cell lines. The PCR product specific for unmethylated DNA in the L and C regions was undetectable or merely faintly present in the same cell lines, suggesting that the cell populations were homogeneously methylated in these regions. Treatment with 5-azacytidine was associated with decreased methylation at the L and C regions in all four cell lines, as evidenced by decreased intensity of the methylation-specific PCR products and de novo or increased expression of the corresponding unmethylated PCR products to equal or greater intensity than the methylated product bands. The susceptibility of KAT-5 and KAT-10 cells to the demethylation effects of 5-azacytidine in the C region appeared less than that of the L region. Although sodium butyrate treatment was associated with re-expression of hNIS mRNA in both NPA'87 and KAT-10, with phenylacetate having a lesser effect in KAT-5, analysis of methylation patterns of the NPA'87 and KAT-10 response to sodium butyrate failed to demonstrate effects on altering baseline methylation patterns in all three regions.

In the three cell lines that failed to express hNIS mRNA, despite treatment with 5-azacytidine, sodium butyrate, or phenylacetate (MRO87, WRO82, and KAT-7), baseline methylation pattern analysis revealed that region P was not methylated while regions L and C were homogeneously methylated. Treatment with 5-azacytidine did not affect the baseline demethylated status in the P region of these cell lines; however the results in the L and C regions were different than seen in the four responding cell lines. Region C appeared methylated under basal conditions in the three cell lines (analysis of WRO82 failed to reveal either methylated or unmethylated products) and did not become demethylated in response to 5-azacytidine, except for minimal detection of an unmethylated product for WRO82 cells (a methylated product becomes clearly visible). The demethylation response, to 5-azacytidine in the L region, was similar in both responsive and non-responsive cell lines. The failure of 5-azacytidine to effectively demethylate the C region distinguished cell lines which failed to re-express hNIS mRNA from those which regained such expression.

Comparison of hNIS Re-expression to Expression Patterns of TTF-1 and PAX-8

To explore the possibility that re-expression of hNIS mRNA may be consequent to re-expression of one or more transcription factor(s) RT-PCR analysis was performed for thyroid-specific transcription factors, TTF-1 and Pax-8 (Table 2). Pax-8 mRNA was found to be expressed under all conditions tested, in all of the four cell lines which were able to re-express hNIS mRNA, while TTF-1 mRNA expression was found even under basal conditions in the cell lines NPA'87 and KAK-1 (data not shown). Basal TTF-1 expression was undetectable in cell lines KAT-5 and KAT-10, although TTF-1 mRNA expression was induced by 5-azacytidine treatment. Likewise, phenylacetate treatment induced TTF-1 mRNA expression only in the KAT-5 cell line, however sodium butyrate did not have such an effect in either of the cell lines.

Example 3

Inhibition of Polyamine Synthesis Restores Sodium/Iodide Symporter Gene Expression and Activity in Dedifferentiated Thyroid Carcinoma Cell Lines hNIS transcriptional failure in thyroid carcinoma could be consequent to methylation of DNA in critical regulatory regions and could be reversed by inhibition of DNA-methyltransferase. Restoration of hNIS gene expression and activity from direct DNA-methyltransferase inhibition by 5-azacytidine has been shown. Reports suggest that decarboxylated S-adenosylmethionine (dcSAM) is an endogenous inhibitor of DNA methylation, competing against the methyl-donor, S-adenosylmethionine. Since dcSAM is consumed by synthesis of polyamines (putrescine, spermidine, spermine) and its synthetic enzyme (adenosylmethionine decarboxylase) is stimulated by polyamine depletion, blockade of polyamine synthesis precipitously increases dcSAM levels. This should block DNA-methyltransferase activity and restore lost hNIS expression in dedifferentiated thyroid carcinomas. To assess this, human thyroid cell lines (NPA'87, papillary carcinoma, & KAK-1, follicular adenoma) without basal expression of hNIS or thyroglobulin (TG) mRNAs, were grown as monolayers in phenol red-free RPMI 1640 with 10% fetal bovine serum. Starting 24 hrs after plating and for 6 days (replacing media & agent every other day), cells were treated with difluoromethylornithine (DFMO, at 1 or 3 mM; an inhibitor of ornithine decarboxylase, blocking putrescine synthesis) or S-adenosyl-1,8-diamino-3-thio-octane (AdoDATO, at 10 or 30 µM; an aminopropyltransferase inhibitor blocking spermidine synthase and spermine synthase). Cells were harvested for RNA, subjected to reverse transcriptase with random hexamer priming for cDNA, and then polymerase chain reactions with primers to amplify: hNIS, TG, thyroid peroxidase (TPO), and β-actin. Parallel cultures were assessed for Na[$^{125}$I] uptake (RAIU) in serum-free buffer, subtracting $^{125}$I counts in buffer with choline (100 mM) to correct for non-specific counts and results normalized for cell density in each condition using thiazolyl blue (MTT) assays. In both cell lines, DFMO and AdoDATO restored hNIS and TG mRNA expression, with higher doses having greater effect. Both cell lines had minimal basal TPO expression with each reagent enhancing expression at every dosage. DFMO at 3 mM caused greatest increases in RAIU (>6-fold) in NPA'87 cells and 30 µM AdoDATO had the greatest response (~5-fold) in KAK-1 cells. This supports DNA-methylation as a reversible cause of loss of iodide transport in dedifferentiated thyroid carcinoma and endorses polyamine inhibition as a therapeutic method to restore responsiveness to radioiodine therapy.

Whereas particular embodiments of this invention have been described above for purposes of illustration, it will be evident to those persons skilled in the art that numerous variations of the details of the present invention may be made without departing from the invention as defined in the appended claims.

All of the references cited herein are incorporated by reference in their entirety.

TABLE 1

| Tumor Histology | Sample Number | Methylation Status by Region | | | hNIS mRNA Expression | Clinical Radioiodine Uptake |
|---|---|---|---|---|---|---|
| | | P | L | C | | |
| Typical papillary Carcinoma | 1 | − | + | + | ++ | + |
| | 2 | − | − | − | − | N.A. |
| | | − | | | | |
| | 3 | + | faint | | + | + |
| | | − | | | | |
| | 4 | − | − | | + | + |
| | | − | | | | |
| | 5 | − | + | + | ++ | N.A. |
| | 6 | ++ | − | + | ++ | + |
| | 7 | ++ | + | ++ | + | + |
| | 8 | − | + | | + | + |
| | | − | | | | |
| | 9 | + | ++ | ++ | + | − |
| | 10 | + | − | | + | − |
| | | − | | | | |
| Tall-cell variant Papillary carcinoma | 11 | ++ | faint | ++ | − | − |
| | 12 | ++ | + | ++ | + | − |
| | 13 | + | + | faint | − | − |
| | 14 | ++ | + | | − | − |
| | | − | | | | |
| | 15 | ++ | + | faint | − | − |
| | 16 | + | − | | + | − |
| | | − | | | | |
| Follicular Carcinoma | 17 | + | faint | | ++ | + |
| | | − | | | | |
| | 18 | − | faint | ++ | ++ | N.A. |
| Hürthle cell Carcinoma | 19 | − | − | + | ++ | − |
| | 20 | − | + | | − | − |
| | | − | | | | |
| | 21 | − | − | ++ | − | − |
| Anaplastic Carcinoma | 22 | ++ | − | + | + | N.A. |
| | 23 | − | − | | ++ | − |
| | | faint | | | | |
| Normal Thyroid Tissue | 24 | faint | − | | ++ | +* |
| | | − | | | | |
| | 25 | faint | − | | ++ | +* |
| | | − | | | | |
| | 26 | − | − | + | ++ | +* |
| | 27 | faint | − | + | ++ | +* |
| | 28 | faint | − | | ++ | +* |
| | | − | | | | |

Methylation: ++, distinctly positive; +, moderately positive; faint, slightly positive; −, negative.

mRNA expression: ++, comparable to normal thyroid; +, moderate level; −, negative.

Clinical radioiodine uptake: +, positive tumor uptake; +*, assumed (patient euthyroid); −, no tumor uptake; N.A., results not available.

TABLE 2

Human thyroid cell line analysis

| Cell Line | Culture Additive | hNIS mRNA | Specific $^{125}$I Uptake | Methylation Status by Region P | L | C | TTF-1 mRNA | Pax-8 mRNA |
|---|---|---|---|---|---|---|---|---|
| NPA'87 | None | − | − | − | + | + | + | + |
|  | AzaC-low | − | − | nd | nd | nd | nd | nd |
|  | AzaC-high | + | + | − | − | − | + | + |
|  | NaB-low | − | − | nd | nd | nd | nd | nd |
|  | NaB-high | + | − | − | + | + | + | + |
|  | PhAc-low | − | − | nd | nd | nd | nd | nd |
|  | PhAc-high | − | − | nd | nd | nd | nd | nd |
| KAK-1 | None | − | − | − | + | + | + | + |
|  | AzaC-low | + | − | − | − | − | + | + |
|  | AzaC-high | + | + | − | − | − | + | + |
|  | NaB-low | − | − | nd | nd | nd | nd | nd |
|  | NaB-high | − | − | nd | nd | nd | nd | nd |
|  | PhAc-low | − | − | nd | nd | nd | nd | nd |
|  | PhAc-high | − | − | nd | nd | nd | nd | nd |
| KAT-5 | None | − | − | − | + | + | − | + |
|  | AzaC-low | − | − | nd | nd | nd | nd | nd |
|  | AzaC-high | + | − | − | − | − | + | + |
|  | NaB-low | − | − | nd | nd | nd | nd | nd |
|  | NaB-high | − | − | nd | nd | nd | nd | nd |
|  | PhAc-low | − | − | nd | nd | nd | nd | nd |
|  | PhAc-high | + | − | − | + | + | + | + |
| KAT-10 | None | − | − | − | + | + | − | + |
|  | AzaC-low | + | − | − | − | − | + | + |
|  | AzaC-high | Lethal additive concentration for this cell line | | | | | | |
|  | NaB-low | − | − | nd | nd | nd | nd | nd |
|  | NaB-high | + | − | − | + | + | − | + |
|  | PhAc-low | − | − | nd | nd | nd | nd | nd |
|  | PhAc-high | − | − | nd | nd | nd | nd | nd |

Culture Additives: AzaC, 5-azacytidine (low, 0.5 µM; high, 1.0 µM); NaB, sodium butyrate (low, 0.5 mM; high, 1.0 mM); and PhAc, phenylacetate (low, 5.0 mM; high, 10 mM).
Specific $^{125}$I uptake (monolayer cultures): +, positive; and −, negative.
Methylation: +, positive, −, negative.
mRNA expression (hNIS, TTF-1, Pax-8): +, positive; −, negative; and nd, not done.

REFERENCES

1. Carrasco N. 1993 Iodide transport in the thyroid gland. Biochim Biophys Acta. 1154:65–82.
2. Robbins J, Merino M J, Boice Jr J D, et al. 1991 Thyroid cancer: a lethal neoplasm. Ann Int Med. 115:133–147.
3. Smanik P A, Liu Q, Furminger T L, et al. 1996 Cloning of the human sodium iodide symporter. Biochem Biophys Res Comm. 226:339–345.
4. Smanik P A, Ryu K-Y, Theil K S, Mazzaferri E L, Jhiang S M. 1997 Expression, exon-intron organization, and chromosome mapping of the human sodium iodide symporter. Endocrinol. 138:3555–3558.
5. Venkataraman G M, Yatin M, Ain K B. 1998 Cloning of the human sodium-iodide symporter promoter and characterization in a differentiated human thyroid cell line, KAT-50. Thyroid. 8:63–69.
6. Behr M, Schmitt T L, Espinoza C R, Loos U. 1998 Cloning of a functional promoter of the human sodium/iodide-symporter gene. Biochem J. 331:359–363.
7. Ryu K-Y, Tong Q, Jhiang S M. 1998 Promoter characterization of the human Na$^+$/I$^-$ symporter. J Clin Endocrinol Metab. 83:3247–3251.
8. Graff J R, Greenberg V E, Herman J G, et al. 1998 Distinct patterns of E-cadherin CpG island methylation in papillary, follicular, Hurthle's cell, and poorly differentiated thyroid carcinoma. Cancer Res. 58:2063–2066.
9. Baylin S B, Herman J G, Graff J R, Vertino P M, Issa J-P. 1998 Alterations in DNA methylation: A fundamental aspect of neoplasia. Adv Cancer Res. 65:141–196.
10. Baylin S B. 1997 Tying it all together: epigenetics, genetics, cell cycle, and cancer. Science. 277:1948–1949.
11. Stirzaker C, Millar D S, Paul C L, et al. 1997 Extensive DNA methylation spanning the Rb promoter in retinoblastoma tumors. Cancer Res. 57:2229–2237.
12. Qian X C, Brent T P. 1997 Methylation hot spots in the 5' flanking region denote silencing of the O$^6$-methylguanine-DNA methyltransferase gene. Cancer Res. 57:36723677.
13. von Wronski M A, Brent T P. 1994 Effect of 5-azacytidine on expression of human DNA repair enzyme O$^6$-methylguanine-DNA methyltransferase. Carcinogenesis. 15:577–582.
14. Samid D, Yeh A, Prasanna P. 1992 Induction of erythroid differentiation and fetal hemoglobin production in human leukemic cells treated with phenylacetate. Blood. 80:1576–1581.
15. Ormandy C J, de Fazio A, Kelly P A, Sutherland R L. 1992 Transcriptional regulation of prolactin receptor gene expression by sodium butyrate in MCF-7 human breast cancer cells. Endocrinol. 131:982–984.
16. Ain K B, Taylor K D, Tofiq S, Venkataraman G. 1997 Somatostatin receptor subtype expression in human thyroid and thyroid carcinoma cell lines. J Clin Endocrinol Metab. 82:1857–1862.

17. Ain K B, Taylor K D. 1994 Somatostatin analogs affect proliferation of human thyroid carcinoma cell lines in vitro. J Clin Endocrinol Metab. 78:1097–1102.
18. Gilbert S F, Migeon B R. 1975 D-Valine as a selective agent for normal human and rodent epithelial cells in culture. Cell. 5:11–17.
19. Kao WW-Y, Prockop D J. 1977 Proline analogue removes fibroblasts from cultured mixed cell populations. Nature. 266:63–64.
20. Yatin M, Venkataraman G M, Taylor K D, Ain K B. 1997 Effects of TSH, insulin, and selenium on iodide uptake and organification in the benign human thyroid follicular hyperplasia cell line, KAT-50. Thyroid. 7:S99.
21. Chomczynski P, Sacchi N. 1987 Single step method of RNA isolation by acid guanidinium thiocyanate-phenol-chloroform extraction. Anal Biochem. 162:156–159.
22. Poleev A, Fickenscher H, Mundlos S, et al. 1992 Pax8, a human paired box gene: isolation and expression in developing thyroid, kidney and Wilms' tumors. Develop. 116:611–623.
23. Wang RY-W, Gehrke C W, Ehrlich M. 1980 Comparison of bisulfite modification of 5-methyldeoxycytidine and deoxycytidine residues. Nucl Acids Res. 8:4777–4790.
24. Herman J G, Graff J R, Myöhänen S, Nelkin B D, Baylin S B. 1996 Methylation-specific PCR: a novel PCR assay for methylation status of CpG islands. Proc Natl Acad Sci USA. 93:9821–9826.
25. Mosmann T. 1983 Rapid colorimetric assay for cellular growth and survival: application to proliferation and cytotoxic assays. J Immunol Methods. 65:55–61.
26. Tong Q, Ryu K Y, Jhiang S M. 1997 Promoter characterization of the rat $Na^+/I^-$ symporter gene. Biochem Biophys Res Commun. 239:34–41.
27. Van Herle A J, Agatep M L, Padua III D N, et al. 1990 Effects of 13 cis-retinoic acid on growth and differentiation of human follicular carcinoma cells (UCLA RO 82 W-1) in vitro. J Clin Endocrinol Metab. 71:755–763.
28. Simon D, Köhrle J, Schmutzler C, Mainz K, Reiners C, Röher H-D. 1996 Redifferentiation therapy of differentiated thyroid carcinoma with retinoic acid: basics and first clinical results. Exp Clin Endocrinol Diabetes. 104:13–15.
29. Simon D, Koehrle J, Reiners C, et al. 1998 Redifferentiation therapy with retinoids: therapeutic options for advanced follicular and papillary thyroid carcinoma. World J. Surg. 22:569–574.
30. Grünwald F, Pakos E, Bender H, et al. 1998 Redifferentiation therapy with retinoic acid in follicular thyroid cancer. J Nucl Med. 39:1555–1558.
31. Misaki T, Miyamoto S, Alam M S, Kasagi K, Konishi J. 1996 Tumoricidal cytokines enhance radioiodine uptake in cultured thyroid cancer cells. J Nucl Med. 37:646–648.
32. Ain K B. 1995 Papillary thyroid carcinoma: etiology, assessment, and therapy. Endocrin Metab Clin N Amer. 24:711–760.
33. Ain K B. 1998 Rare forms of thyroid cancer. In Thyroid Cancer. Fagin JA, ed. Boston, Mass.: Kluwer Academic Publishers; 319–340.
34. Caillou B, Troalen F, Baudin E, et al. 1998 $Na^+/I^-$ symporter distribution in human thyroid tissues: an immunohistochemical study. J Clin Endocrinol Metab. 83:4102–4106.
35. Jhiang S M, Cho J-Y, Ryu K-Y, et al. 1998 An immunohistochemical study of $Na^+/I^-$ symporter in human thyroid tissues and salivary gland tissues. Endocrinol. 139:4416–4419.
36. Elisei R, Shiohara M, Koeffler H P, Fagin JA. 1998 Genetic and epigenetic alterations of the cyclin-dependent kinase inhibitors p15INK4b and p16INK4a in human thyroid carcinoma cell lines and primary thyroid carcinomas. Cancer. 83:185–193.
37. Chun Y S, Saji M, Zeiger M A. 1998 Overexpression of TTF-1 and PAX-8 restores thyroglobulin gene promoter activity in ARO and WRO cell lines. Surgery. 124:1100–1105.
38. Zannini M, Avantaggiato V, Biffali E, et al. 1997 TTF-2, a new forkhead protein, shows a temporal expression in the developing thyroid which is consistent with a role in controlling the onset of differentiation. EMBO J. 16:3185–3197.
39. Chadwick B P, Obermayr F, Frischauf A M. 1997 FKHL15, a new human member of the forkhead gene family located on chromosome 9q22. Genomics. 41:390–396.
40. Ohmori M, Endo T, Harii N, Onaya T. 1998 A novel thyroid transcription factor is essential for thyrotropin-induced up-regulation of Na+/I– symporter gene expression. Mol Endocrinol. 12:727–736.
41. Ledent C, Parmentier M, Vassart G. 1990 Tissue-specific expression and methylation of a thyroglobulin-chloramphenicol acetyltransferase fusion gene in transgenic mice. Proc Natl Acad Sci USA. 87:6176–6180.
42. Ikuyama S, Niller HH, Shimura H, Akamizu T, Kohn L D. 1992 Characterization of the 5'-flanking region of the rat thyrotropin receptor gene. Mol Endocrinol. 6:793–804.
43. Avvedimento EV, Obici S, Sanchez M, Gallo A, Musti A, Gottesman M E. 1989 Reactivation of thyroglobulin gene expression in transformed thyroid cells by 5-azacytidine. Cell. 58:1135–1142.
44. Avvedimento VE, Musti AM, Ueffing M, et al. 1991 Reversible inhibition of a thyroid-specific trans-acting factor by Ras. Genes Develop. 5:22–28.
45. Pochin E E. 1971 Radioiodine therapy of thyroid cancer. Sem Nucl Med. 1:503–515.
46. Schlesinger T, Flower M A, McCready VR. 1989 Radiation dose assessments in radioiodine ($^{131}$I) therapy. 1. The necessity for in vivo quantitation and dosimetry in the treatment of carcinoma of the thyroid. Radiother Oncol. 14:35–41.
47. Benua R S, Leeper R D. 1986 A method and rationale for treating metastatic thyroid carcinoma with the largest safe dose of $^{131}$I. In Medeiros-Neto G, Gaitan E, ed. Frontiers in Thyroidology ed). New York: Plenum Medical Book Co; 1317–1321
48. Shimura H, Haraguchi K, Miyazaki A, Endo T, Onaya T. 1997 Iodide uptake and experimental $^{131}$I therapy in transplanted undifferentiated thyroid cancer cells expressing the $Na^+/I^-$ symporter gene. Endocrinology. 138:4493–4496.
49. U.S. Pat. No. 6,015,376
50. Archer S Y, Hodin R A. Histone acetylation and cancer. Curr Opin Genet Dev. 1999 Apr.;9(2):171–4. Review. PMID: 10322142; UI: 99257411
51. Doenecke D, Gallwitz D. Acetylation of histones in nucleosomes. Cell Biochem. 1982 Apr. 30;44(2):113–28. Review. No abstract available. PMID: 6808351; UI: 82245291
52. Kruh J. Effects of sodium butyrate, a new pharmacological agent, on cells in culture. Mol Cell Biochem. 1982 Feb. 5;42(2):65–82. Review. PMID: 6174854; UI: 82148201

53. Pollard K J, Samuels M L, Crowley K A, Hansen J C, Peterson C L. Functional interaction between GCN5 and polyamines: a new role for core histone acetylation. EMBO J. 1999 Oct. 15;18(20):5622–33. PMID: 10523306; UI:
54. Matthews H R. Polyamines, chromatin structure and transcription. Bioessays. 1993 Aug.;15(8):561–6. Review. PMID: 8135771; UI: 94183195
55. Spencer V A, Davie J R. Role of covalent modifications of histones in regulating gene expression. Gene. 1999 Nov. 15;240(1):1–12. Review. PMID: 10564807; UI: 20033543
56. Davie J R, Chadee D N. Regulation and regulatory parameters of histone modifications. J Cell Biochem Suppl. 1998;30–31:203–13. Review. PMID: 9893272; UI: 99109150

What is claimed is:

1. A method for introducing iodide into a human thyroid carcinoma cell containing a silenced endogenous gene encoding human sodium/iodide symporter comprising administering to the cell a compound selected from the group consisting of 5-azacytidine, sodium butyrate, dimethylsulfoxide, adenosyl-1,8-diamino-3-thio-octane, and phenylacetate; and administering to the cell radiolabeled iodide.

2. The method of claim 1 wherein the thyroid carcinoma cell is a thyroid typical papillary carcinoma cell or a follicular carcinoma.

3. The method of claim 1, wherein the compound is sodium butyrate.

4. The method of claim 1 wherein the compound is dimethylsulfoxide.

5. The method of claim 1 wherein the compound is adenosyl-1,8-diamino-3-thio-octane.

6. The method of claim 1 wherein the compound is phenylacetate.

7. The method of claim 1 wherein the compound is 5-azacytidine.

8. A method for restoring iodide transport to a human thyroid carcinoma cell comprising administering 5-azacytidine to the cell in an amount effective to transcriptionally activate the expression of a gene encoding the human sodium/iodide symporter.

9. A method of restoring iodide transport to a human thyroid carcinoma cell comprising administering difluoromethylornithine or adenosyl-1,8-diamino-3-thio-octane to the cell in an amount effective to transcriptionally activate the expression of a gene encoding the human sodium/iodide symporter, and administering to the cell radiolabeled iodide.

10. The method of claim 9 wherein difluoromethylornithine is administered.

* * * * *